(12) United States Patent
Boe

(10) Patent No.: US 9,017,074 B2
(45) Date of Patent: Apr. 28, 2015

(54) DENTAL PROSTHETIC DEVICE WITH REMOLDABLE BASE

(75) Inventor: Irwin N. Boe, Leawood, KS (US)

(73) Assignee: Innovative Products, Inc., Leawood, KS (US)

( * ) Notice: Subject to any disclaimer, the term of this patent is extended or adjusted under 35 U.S.C. 154(b) by 80 days.

(21) Appl. No.: 13/385,381

(22) Filed: Feb. 16, 2012

(65) Prior Publication Data

US 2012/0258426 A1 Oct. 11, 2012

Related U.S. Application Data

(63) Continuation-in-part of application No. 13/066,202, filed on Apr. 8, 2011, now abandoned.

(51) Int. Cl.
| *A61C 13/00* | (2006.01) |
| *A61C 13/01* | (2006.01) |
| *A61C 13/093* | (2006.01) |

(52) U.S. Cl.
CPC ............. *A61C 13/01* (2013.01); *A61C 13/1006* (2013.01)

(58) Field of Classification Search
CPC .. A61C 13/01; A61C 13/1006; A61C 13/105; A61C 13/08; A61C 13/225; A61C 13/24; A61C 13/0025; A61C 13/00; A61C 13/267
USPC .................................................. 433/169–171
See application file for complete search history.

(56) References Cited

U.S. PATENT DOCUMENTS

| 1,367,885 | A | * | 2/1921 | Means | 433/169 |
| 3,413,722 | A | * | 12/1968 | Skinner | 433/169 |
| 3,667,123 | A | * | 6/1972 | Huey | 433/171 |
| 3,727,309 | A | * | 4/1973 | Huey | 433/171 |
| 3,813,777 | A | * | 6/1974 | Van Handel et al. | 433/171 |
| 3,813,778 | A | * | 6/1974 | Van Handel | 433/169 |
| 4,247,287 | A | * | 1/1981 | Gigante | 433/199.1 |
| 4,376,629 | A | * | 3/1983 | Ebeling | 433/199.1 |
| 4,654,006 | A | | 3/1987 | Kusano et al. | |
| 4,923,795 | A | * | 5/1990 | Franklin | 433/168.1 |
| 5,630,717 | A | * | 5/1997 | Zuest et al. | 433/172 |
| 6,431,865 | B1 | * | 8/2002 | Uji | 433/169 |
| 7,699,610 | B2 | | 4/2010 | Childress | |
| 7,806,691 | B2 | * | 10/2010 | Berger | 433/172 |
| 2007/0009852 | A1 | * | 1/2007 | Childress | 433/167 |
| 2010/0099058 | A1 | * | 4/2010 | Wang | 433/173 |

* cited by examiner

*Primary Examiner* — Cris L Rodriguez
*Assistant Examiner* — Mirayda A Aponte
(74) *Attorney, Agent, or Firm* — Mashburn Law Office LLC; Donna Denise Mashburn

(57) ABSTRACT

A dental prosthetic device (10,110) having a base (12,112) constructed of an inexpensive remoldable material, such as, for example, ethylene vinyl acetate, to allow for inexpensive and quick fitting and refitting to accommodate changes in dental structure (122). Harder teeth-like structures (14,114) are associated with a mounting surface (20,120) of the base (12,112), such as by overmolding the base (12,112) onto ends (38) of the structures (14,114), so that, when the device (10, 110) is placed over a dental arch (122) within a user's mouth, the teeth-like structures (14,114) facilitate biting and chewing in the manner of teeth.

16 Claims, 6 Drawing Sheets

DENTAL PROSTHETIC DEVICE WITH REMOLDABLE BASE

RELATED APPLICATIONS

The present U.S. non-provisional patent application is a continuation-in-part of an earlier-filed application of the same title, Ser. No. 13/066,202, filed Apr. 8, 2011 now abandoned. The contents of the identified earlier-filed application are hereby incorporated by reference into the present application. To the greatest extent possible, the applicant hereby rescinds and disclaims any arguments, admissions, or other statements or actions, whether implied or expressed, that may have given rise to prosecution history estoppel in the identified earlier-filed application or any other related applications.

BACKGROUND OF THE INVENTION

1. Technical Field

The present invention relates to dental prosthetic devices, including full and partial dentures. More specifically, the present invention concerns a dental prosthetic device having a softer base component comprising a remoldable material, such as a thermoplastic material, which conforms to at least a portion of a dental arch, and a harder component comprising one or more teeth-like structures embedded or otherwise associated with a mounting surface of the softer base component.

2. Background

Dental prosthetics, which include partial and complete dentures, can help people in many ways, including improving their appearance and self-esteem as well as their ability to chew food and speak clearly. The usefulness of dental prosthetics is reflected in their at least 2700 year history, during which time they were made of materials such as bone and wood.

Modern dental prosthetics, especially the base component which contacts the dental arch, are commonly made of acrylic, other hard plastics, or metal and can require several initial appointments over one or two months to construct and achieve a proper fit and appearance, and periodic adjustments to maintain a proper fit as the shapes of users' dental tissues change. For example, following an extraction of many or all teeth, tissue and bone may take many months to heal, and, during that time, prior art dental prosthetics can suffer problems with support, stability, and retention, and can create sore spots on soft tissue because of changing fit. Furthermore, the underlying bones, particularly the mandibular arch, can continue changing for many years and require periodic refittings, possibly as often as every five to seven years. For these and other reasons, modern dental prosthetics can be prohibitively expensive for some people.

Due to these and other problems and disadvantages in the prior art, a need exists for a dental prosthetic device that is less expensive to make, fit, and maintain.

SUMMARY OF THE INVENTION

The present invention overcomes the above-identified and other problems and disadvantages by providing a dental prosthetic device having a base constructed of an inexpensive remoldable material, such as, for example, ethylene vinyl acetate, to allow for inexpensive and quick fitting and refitting to accommodate changes in dental structure.

Broadly, the dental prosthetic device comprises a softer base component constructed of the remoldable material and having a contact surface and a mounting surface, with the contact surface being shaped to fit over a dental arch; and a harder component comprising one or more teeth-like structures associated with the mounting surface of the softer component, wherein, when the dental prosthetic device is placed over the dental arch within a user's mouth, the harder component facilitates biting and chewing in the manner of teeth.

In various implementations, the device may further comprise any one or more of the following features. The softer base component may be constructed of a remoldable elastomeric material. The softer base component may be constructed of a remoldable thermoplastic material, such as ethylene vinyl acetate, which, when warmed to a relatively low temperature, such as, for example, approximately 105 degrees C. or lower, between 85 degrees C. and 105 degrees C., between 65 degrees C. and 85 degrees C., or lower than 65 degrees C., is conformable to the dental arch. The harder component may be constructed of a molded acrylic material. The one or more teeth-like structures of the harder component may be embedded in the softer component, such as, for example, by overmolding the softer base component onto ends of the one or more teeth-like structures. The softer base component may be colored to resemble gum tissue. The one or more teeth-like structures of the harder component may be shaped and colored to resemble teeth. The device may further include an intermediate component positioned approximately between the softer base and harder components in order to, for example, better support the teeth-like structures.

In another embodiment, the dental prosthetic device may comprise the softer base component constructed of the remoldable thermoplastic material including ethylene vinyl acetate which, when warmed to approximately between 50 degrees C. and 105 degrees C., is conformable to the dental arch, the softer base component having the contact surface and the mounting surface, with the contact surface having a center portion shaped to fit against an oral palate and at least one sidewall shaped to fit over the dental arch, and the softer base component being colored to resemble gum tissue; and the harder component including the one or more tooth-like structures partially embedded in the softer base component and extending beyond the mounting surface of the softer base component, and the one or more tooth-like structures being shaped and colored to resemble teeth, and one or more internal support structures (resembling ribs or fingers or material) connected to the one or more tooth-like structures and embedded in and extending at least half-way into the center portion and at least half-way into the at least one sidewall of the softer base component, wherein, when the dental prosthetic device is placed within the user's mouth, the device facilitates biting and chewing in the manner of natural teeth.

These and other features of the present invention are discussed in greater detail in the section below entitled DETAILED DESCRIPTION OF THE INVENTION.

BRIEF DESCRIPTION OF THE DRAWINGS

The present invention is described herein with reference to the following drawing figures, which are not necessarily to scale.

DETAILED DESCRIPTION OF THE INVENTION

Figure 1:
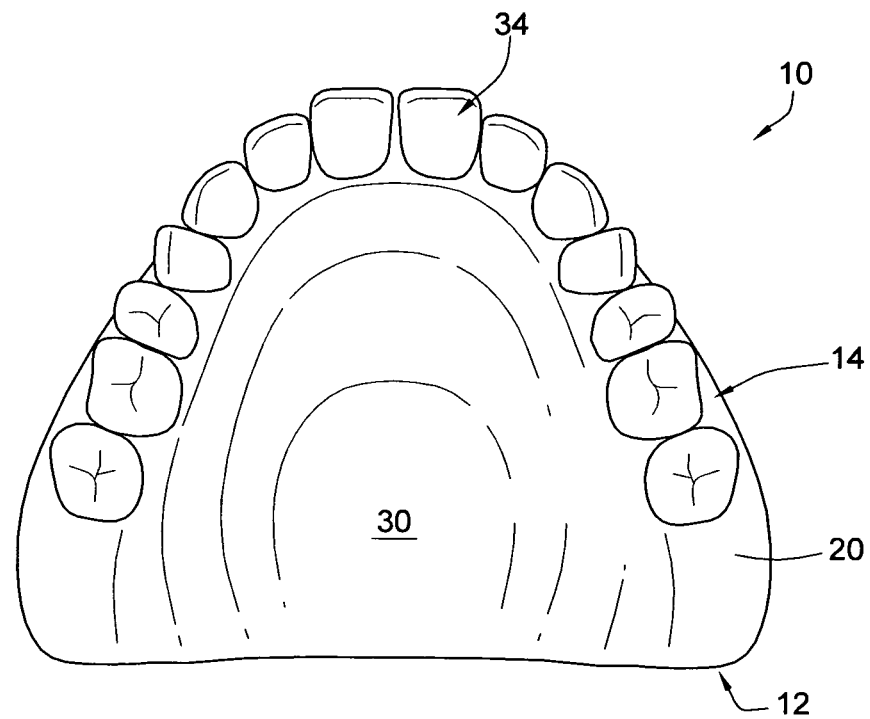
FIG. 1 is a plan view of an upper or maxillary dental prosthetic device of the present invention.
Figure 2:
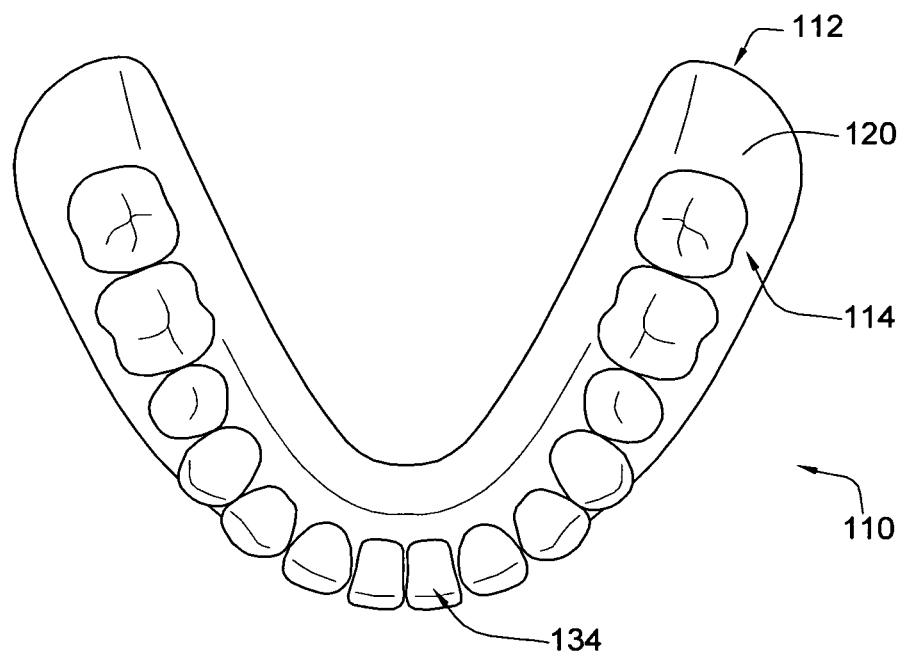
FIG. 2 is a plan view of a lower or mandibular dental prosthetic device of the present invention.
Figure 3:
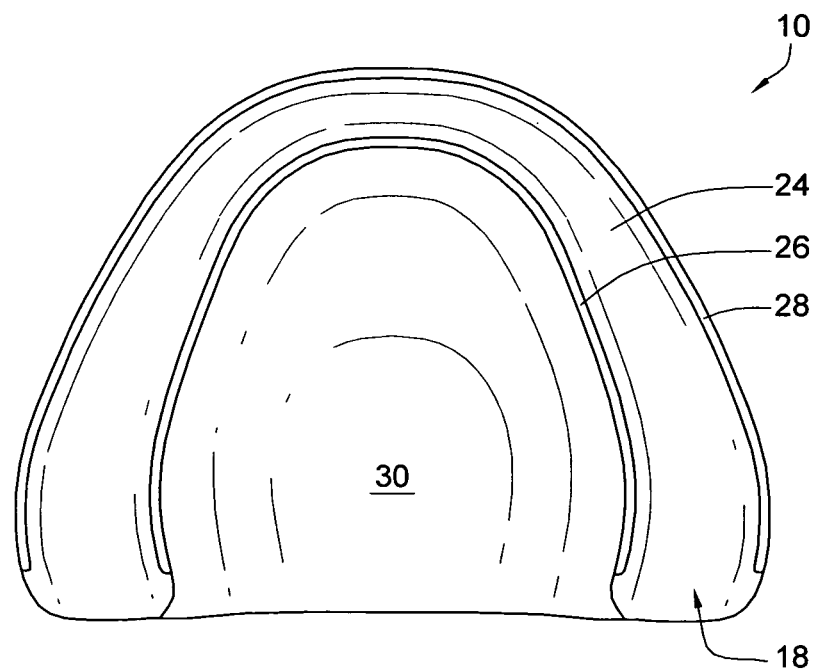
FIG. 3 is a view of a contact surface of the dental prosthetic device of FIG. 1.
Figure 4:
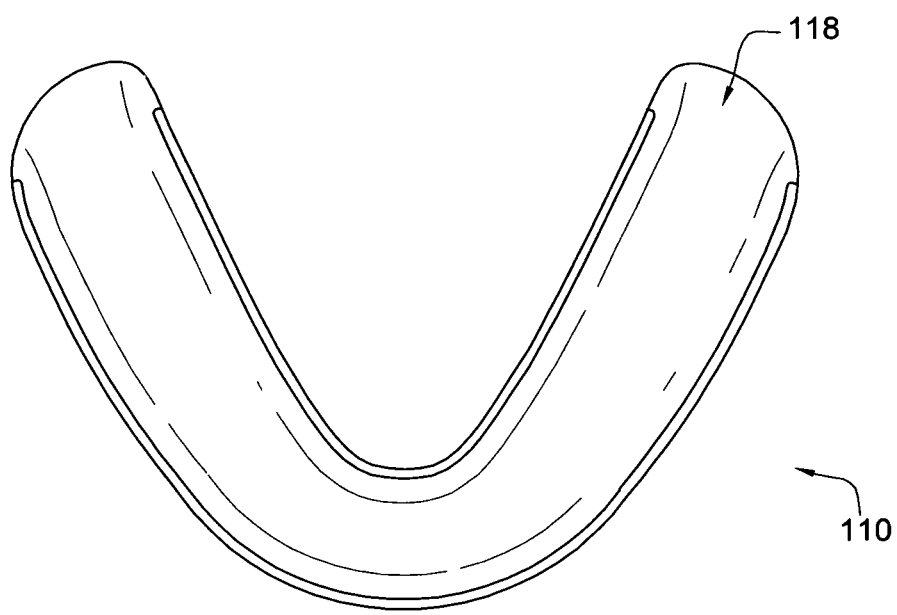
FIG. 4 is a view of a contact surface of the dental prosthetic device of FIG. 1.

With reference to the figures, a dental prosthetic device 10 is herein described, shown, and otherwise disclosed in accordance with one or more embodiments of the present invention, including one or more preferred embodiments. FIGS. 1 and 3 show the dental prosthetic device 10 adapted for an upper or maxillary arch, while FIGS. 2 and 4 show the dental prosthetic device 110 adapted for a lower or mandibular arch. The upper and lower adaptations of the device 10,110 may be substantially identical with regard to materials and method of construction, unless noted.

Figure 6:
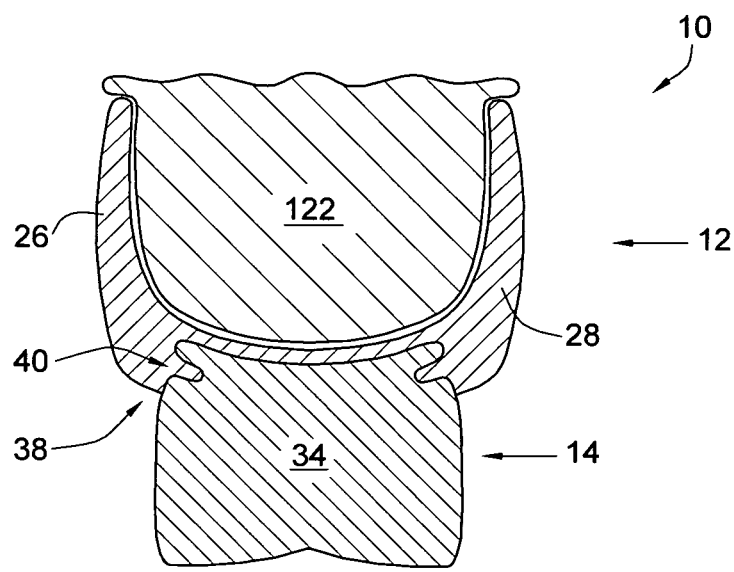
FIG. 6 is a cross-sectional elevation view of the dental prosthetic device of the present invention showing its functional relation to a dental arch.
Figure 5:
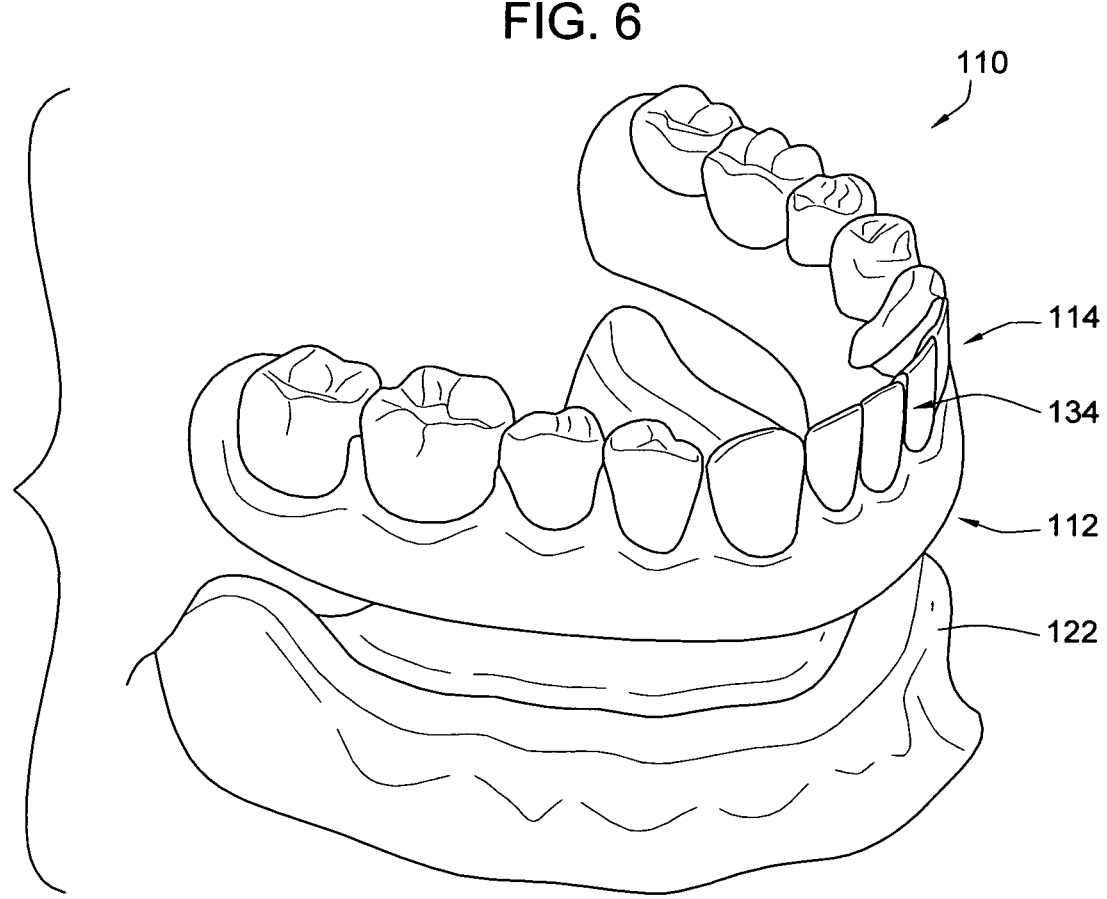
FIG. 5 is a partially exploded perspective view of the dental prosthetic device of FIG. 2, showing its functional relation to a mandibular arch.

Broadly, the dental prosthetic device 10,110 comprises a softer base component 12,112 and a harder component 14,114. The softer base component 12,112 includes a contact surface 18,118 and a mounting surface 20,120. Referring also to FIGS. 5 and 6, the contact surface 18,118 is generally shaped to fit over the dental arch 122. More specifically, the contact surface 18,118 may be generally channel-shaped with a groove 24 running between inner and outer sidewalls 26,28, so that the dental arch 122 is at least partially received within the groove 24. The maxillary version of the device 10 may include a center portion 30, as shown in FIG. 1, or may exclude the center portion and be substantially U-shaped like the mandibular version 110 shown in FIG. 2.

The softer base component 12,112 may incorporate a remoldable elastomeric or thermoplastic material, such as, for example, ethylene vinyl acetate, which, when activated, such as by being warmed at ambient pressure to a relatively low temperature, such as, for example, approximately 105 degrees C. or lower, between 85 degrees C. and 105 degrees C., between 50 degrees C. and 85 degrees C., or lower than 50 degrees C., conforms more closely to the dental arch 122. More specifically, a relatively close fit can be achieved by warming or otherwise activating the softer base component 12,112 and placing the contact surface 18,118 over the dental arch 122 so that the material of the softer base component more closely conforms to the shape of the dental arch 122. Furthermore, the softer base component 12,112 can be rewarmed or reactivated whenever necessary or desirable to remold it to the changing shape of the dental arch 122. The softer base component 12,112 may be colored to, for example, resemble gum tissue appropriate to the user's race.

The harder component 14,114 includes one or more tooth-like structures 34,134 associated with the mounting surface 20,120 of the softer base component 12,112 such that, when the dental prosthetic device 10,110 is placed within a user's mouth in the manner of a denture, the harder component 14,114 facilitates biting, chewing, and speaking in the manner of natural teeth. The harder component 14,114 may incorporate a molded acrylic material. The one or more tooth-like structures 34,134 may be affixed to or, as shown in FIG. 6, embedded in the softer base component 12,112, such as, for example, by overmolding the softer base component 12,112 onto ends 38 of the one or more tooth-like structures 34,134. The ends 38 of the one or more tooth-like structures 34,134 may be provided with grooves, holes, or other features 40 to better maintain their relationship with the softer base component 12,112. The one or more tooth-like structures 34,134 may be shaped and colored to resemble natural teeth, or may be shaped and/or colored in substantially any manner of functionally or aesthetically desirable ways.

The dental prosthetic device 10,110 may be produced in a limited number of sizes, such as, for example, small, medium, and large, which provides a first order of fit. Heating or otherwise activating the softer base component 12,112 and molding it to the user's particular dental arch provides a second order of fit. As discussed, the user can thereafter reheat or otherwise reactivate the soft base component 12,112 to refit the device 10,110 whenever necessary due, for example, to changing tissue shape.

In one exemplary embodiment incorporating certain of the aforementioned features, the dental prosthetic device 10,110 may comprise the softer base component 12,112 being constructed of a remoldable material and having the contact surface 18,118 and the mounting surface 20,120, with the contact surface 18,118 being shaped to fit over the dental arch 122, and the softer base component 12,112 being colored to resemble gum tissue; and the harder component 14,114 comprising the one or more tooth-like structures 34,134 partially embedded in the softer base component 12,112 and extending beyond the mounting surface 20,120 of the softer base component 12,112, and the one or more tooth-like structures 34,134 being shaped and colored to resemble natural teeth, wherein, when the dental prosthetic device 10,110 is placed within a user's mouth, the harder component 14,114 facilitates biting and chewing in the manner of natural teeth.

In another exemplary embodiment incorporating certain of the aforementioned features, the dental prosthetic device 10,110 may comprise the softer base component being constructed of a remoldable thermoplastic material which, when warmed, conforms more closely to the dental arch 122, the softer base component 12,112 having the contact surface 18,118 and the mounting surface 20,120, with the contact surface 18,118 being shaped to fit over the dental arch 122, and the softer base component 12,112 being colored to resemble gum tissue; and the harder component 14,114 comprising one or more tooth-like structures 34,134 constructed of a molded acrylic material embedded in the softer base component 12,112 and extending beyond the mounting surface 20,120 of the softer base component 12,112, and the one or more tooth-like structures being shaped and colored to resemble natural teeth, wherein, when the dental prosthetic device 10,110 is placed within a user's mouth, the harder component 14,114 facilitates biting and chewing in the manner of natural teeth.

Figure 7:
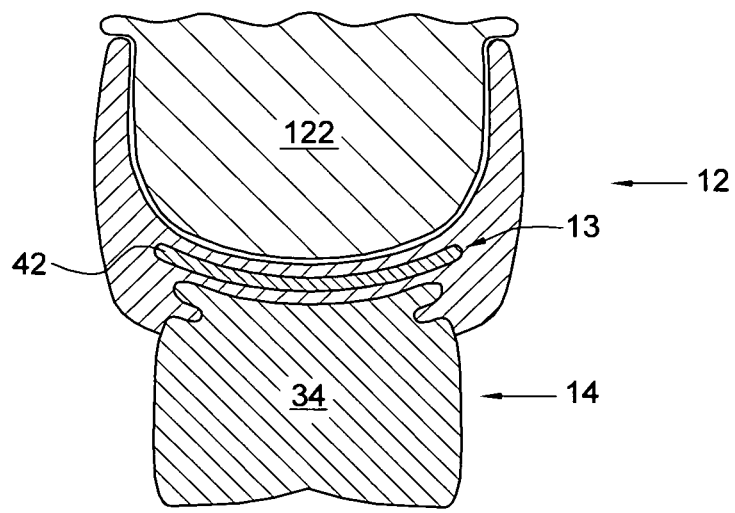
FIG. 7 is a cross-sectional elevation view of the dental prosthetic device of the present invention showing a first form of an intermediate component.
Figure 8:
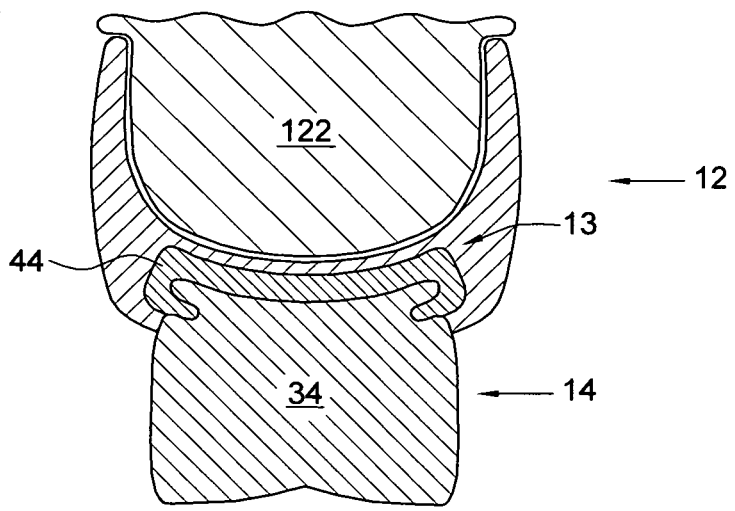
FIG. 8 is a cross-sectional elevation view of the dental prosthetic device of the present invention showing a second form of an intermediate component.

Referring also to FIGS. 7 and 8, the dental prosthetic device 10,110 may further comprise an intermediate component 13 positioned approximately between the softer base component 12,112 and the harder component 14,114. The intermediate component 13 may be constructed of a harder material than the softer base component 12,112 in order, for example, to provide greater durability or wear-resistance or to better maintain or secure the harder component 14,114 relative to the softer base component 12,112. Thus, the intermediate component 13 may be constructed of, for example, a harder version of the material of the softer base component 12,112, a material having a hardness which is intermediate to that of the softer base component 12,112 and the harder component 14,114, or a hardness which is as hard or harder than the hardness of the harder component 14,114. Furthermore, the intermediate component 13 may take a first form 42 in which it touches or does not touch (as shown in FIG. 7) one or both of the other components 12,112,14,114, or may take a second form 44 in which it engages one or both of the other components 12,112,14,114 (as shown in FIG. 8).

Figure 9:
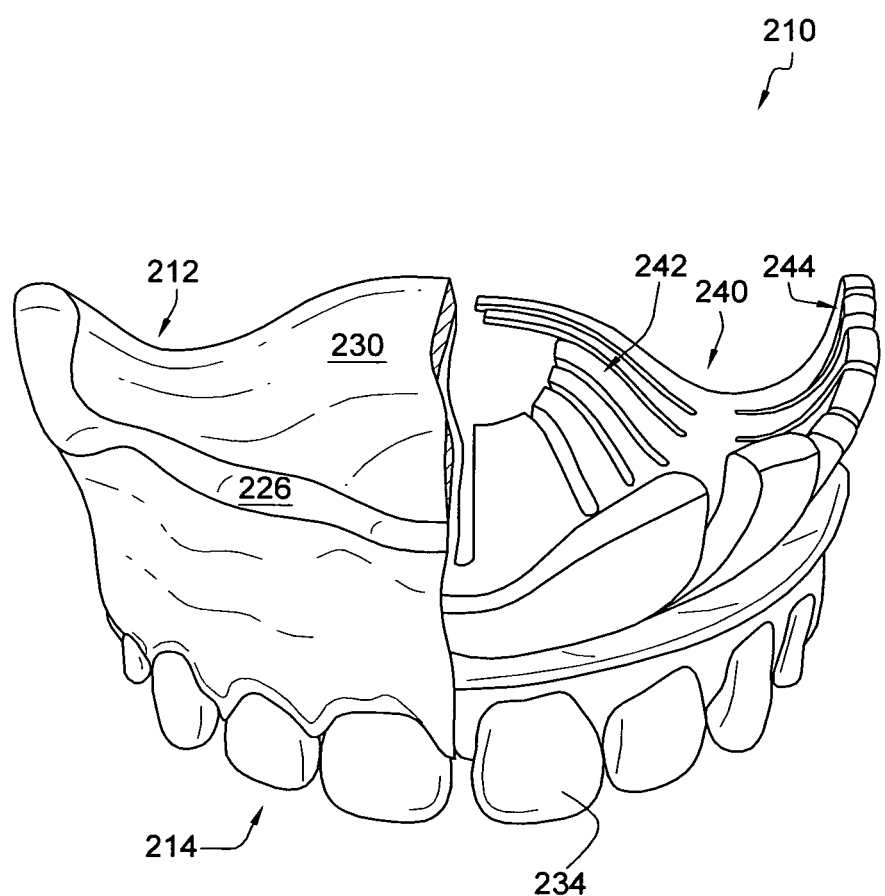
FIG. 9 is a partial cross-sectional perspective view of a second embodiment of the dental prosthetic device showing internal support structures.
Figure 10:
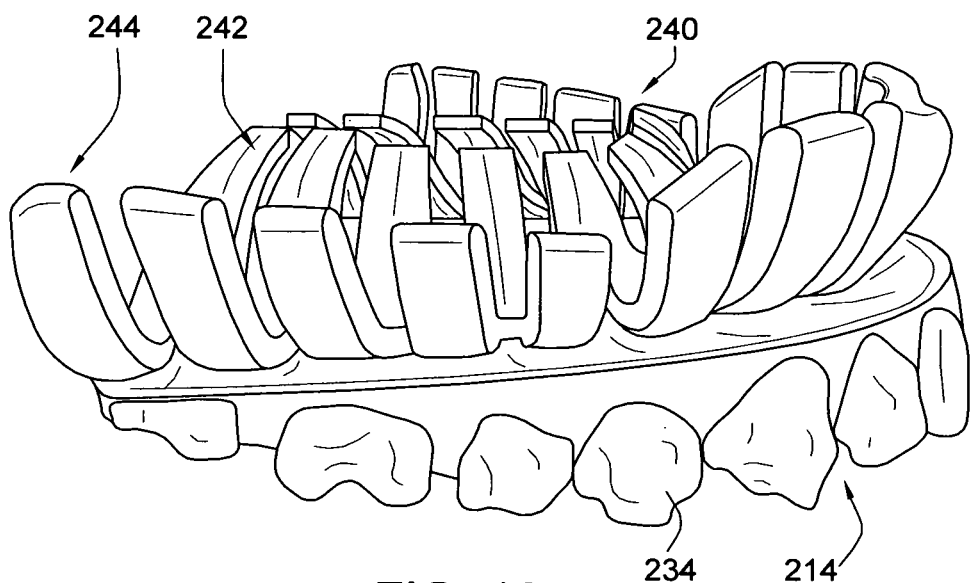
FIG. 10 is a side elevation view of the embodiment of FIG. 9 showing the internal support structures.
Figure 11:
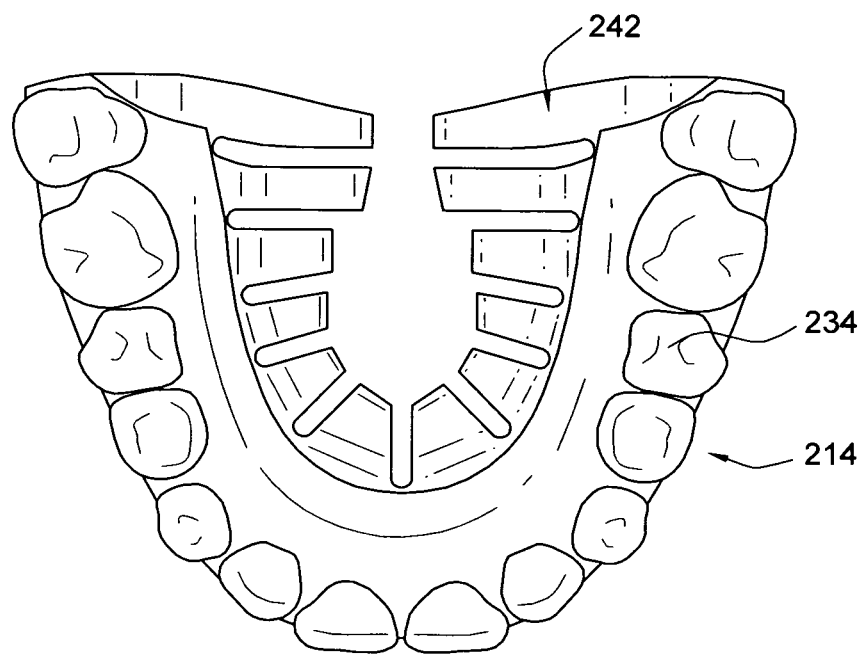
FIG. 11 is a bottom view of the embodiment of FIG. 9 showing the internal support structures.

With reference to FIGS. 9, 10, and 11, a second embodiment of the dental prosthetic device 210 is now described, shown, and otherwise disclosed. The second embodiment may be substantially similar or identical to the first embodiment except as follows. Although the device 210 is shown only adapted for the upper or maxillary arch, it will be appreciated that the following may apply also to the device as adapted for the lower or mandibular arch.

Broadly, the second embodiment of the dental prosthetic device 210 comprises the softer base component 212 and the harder component 214 as discussed above. The harder component 214 includes the one or more tooth-like structures 234 and one or more internal support structures 240 that are embedded within the softer base component 212 and may function to support the tooth-like structures 234 in relation to the softer base component 212 or to achieve or maintain a better fit within the user's mouth.

More specifically, as best seen in FIG. 9, the internal support structures 240 may take the form of ribs or fingers of material extending from the tooth-like structures 234 into the center portion 230 and/or the sidewall(s) 226 (which are best seen in FIG. 6 as reference numerals 26 and 28) of the device 210 and covered by (e.g., overmolded with) the softer base component 212, thereby providing increased support while still benefiting from the remoldability of the softer base component 212. The center portion internal support structures 242 extend into the center portion of the maxillary version of the device 210, and may be sufficiently flexible to substantially conform to differently shaped (e.g., rounder or flatter) palates. The sidewall internal support structures 244 extend into the inner and/or outer sidewalls 26,28 of either the maxillary or the mandibular versions of the device 210 and, again, may be sufficiently flexible to substantially conform to differently shaped dental arches. In both cases, the internal support structures 240 may extend at least half-way, between half-way and three-quarters of the way, or substantially all of the way (possibly even joining at the apex of the center portion) into the center portion 230 and at least half-way, between half-way and three-quarters of the way, or substantially all of the way into the sidewall(s) 226 for better support. In various implementations, there may a single internal support structure, one internal support structure shared by several of the tooth-like structures, or one internal support structure for each of the tooth-like structures.

The tooth-like structures 234 may be made of acrylic or of a more flexible or softer material such as polyethylene or polycarbonate. The latter softer materials may wear faster than the former harder material, but it is anticipated that the relatively low cost of the device 210 (as compared to traditional dentures) will allow for more frequent replacement. The internal support structures 240 may be constructed of the same material as, a more flexible or softer version of the material of, or a different material than the tooth-like structures 234. In particular, at least a flexible or softer version of the material of the tooth-like structure may be desirable to minimize the risk that the internal support structures 240 may tear through the softer base component 212 in which they are embedded and come into direct contact with the user's oral tissues. Relatedly, the tooth-like structures 234 and the internal support structures 240 may be molded or otherwise formed simultaneously or at different times or as a single piece or as multiple pieces.

In one implementation, for example, the tooth-like structures 234 and the internal support structures 240 are molded simultaneously as a single piece but the tooth-like structures 234 are constructed of a harder version of a material (e.g., acrylic) and the internal support structures are constructed of a softer or more flexible version of the material. This may be accomplished, for example, by creating a continuous gradient of one or more additive materials in the mold such that little or none of the additive material(s) is present in the portion of the mold corresponding to the tooth-like structures 234 and more of the additive material(s) is present in the portion of the mold corresponding to the internal support structures 240, resulting in a gradient of hardness of other characteristic(s) from the harder and/or relatively inflexible tooth-like structures 234 to the softer and/or relatively flexible internal support structures 240. Such a gradient may be created, for example, through careful positioning or orientation of the mold, the use of gravity to separate heavier or denser material from lighter or less dense material, or by creating the device 210 from the tooth-like structures 234 to the internal support structures 240 and slowly introducing more of the additive material into the latter once the former has partially cured or will otherwise no longer accept the additional additive material.

Although the invention has been disclosed with reference to various particular embodiments, it is understood that equivalents may be employed and substitutions made herein without departing from the scope of the invention as recited in the claims.

Having thus described the preferred embodiment of the invention, what is claimed as new and desired to be protected by Letters Patent includes the following:

Having thus described the preferred embodiment of the invention, what is claimed as new and desired to be protected by Letters Patent includes the following:

1. A dental prosthetic device comprising:
  a softer base component formed of and constructed by a remoldable material, having a contact surface and a mounting surface, with the contact surface having at least one sidewall shaped to fit over a first dental arch, including a center portion interior to said at least one sidewall, and presenting a first configuration, wherein the softer base component is colored to resemble gum tissue, and the material is facilely remoldable to a second dental arch after the device has been donned, so as to cause the material to adopt a second configuration; and
  a harder component including:
  one or more tooth-like structures partially embedded in the softer base component and extending beyond the mounting surface of the softer base component, wherein said one or more tooth-like structures are shaped and colored to resemble teeth, and
  one or more internal support structures presenting planar ribs, fixedly connected to and radially extending from each of said one or more tooth-like structures, wherein the ribs are embedded in and extend at least half-way into said at least one sidewall of the softer base component, and at least half-way into the center portion of the softer component, wherein, when the dental prosthetic device is donned, the dental prosthetic device facilitates biting and chewing in the manner of natural teeth, wherein the softer base component further includes a center portion shaped to fit against an oral palate, and the one or more internal support structures are embedded in and extend at least half-way into the center portion of the softer base component.

2. The dental prosthetic device as set forth in claim 1, wherein the softer base component is constructed of a remoldable elastomeric material.

3. The dental prosthetic device as set forth in claim 1, wherein the softer base component is constructed of a remoldable thermoplastic material which, when warmed, is conformable to the dental arch.

4. The dental prosthetic device as set forth in claim 3, wherein the thermoplastic material includes ethylene vinyl acetate.

5. The dental prosthetic device as set forth in claim 1, wherein the internal support structures are constructed of a more flexible material than the one or more tooth-like structures.

6. A. dental prosthetic device comprising:
a softer base component formed of and constructed by a remoldable material, having a contact surface and a mounting surface, with the contact surface having at least one sidewall shaped to fit over a first dental arch, including a center portion interior to said at least one sidewall, and presenting a first configuration, wherein the softer base component is colored to resemble gum tissue, and the material is facilely remoldable to a second dental arch after the device has been donned, so as to cause the material to adopt a second configuration: and
a harder component including;
one or tooth-like structures partially embedded in the softer base component and extending beyond the mounting surface of the softer base component, wherein said one or more tooth-like structures are-shaped and colored to resemble teeth, and
one or more internal support structures presenting planer ribs, fixedly connected to and radially extending from each of said one or more tooth-like structures wherein the ribs are embedded in and extend at least half-way into said at least one sidewall of the softer base component, and at least half-way into the center portion of the softer component,
wherein, when the dental prosthetic device is donned, the dental prosthetic device facilitates biting end chewing in the manner of natural teeth,
wherein the one or more tooth-like structures and the one or more internal support structures are constructed of the same material.

7. The dental prosthetic device as set forth in claim 6, wherein the material is polycarbonate.

8. A dental prosthetic device comprising:
a softer base component formed of and constructed by a rcmoldable material, having a contact surface and a mounting surface, with the contact surface having at least one sidewall shaped to fit over a first dental arch, including a center portion interior to said at least one sidewall, and presenting a first configuration, wherein the softer base component is colored to resemble gum tissue, and the material is facilely remoldable to a second dental arch after the device has been donned, so as to cause the material to adopt a second configuration; and
a harder component including:
one or more tooth-like structures partially embedded in the softer base component and extending beyond the mounting surface of the softer base component, wherein said one or more tooth-like structures are-shaped and colored to resemble teeth, and
one or more internal support structures presenting planar ribs, fixedly connected to and radially extending from each of said one or more tooth-like structures, wherein the ribs are embedded in and extend at least half-way into said at least one sidewall of the softer base component, and at least half-way into the center portion of the softer component,
wherein, when the dental prosthetic device is donned, the dental prosthetic device facilitates biting and chewing in the manner of natural teeth,
wherein the one or more tooth-like structures and the one or more internal support structures are molded as a single piece but in such a way as to have different properties, with the one or more internal support structures being more flexible than the one or more tooth-like structures.

9. A dental prosthetic device comprising:
a softer base component constructed of a remoldable thermoplastic material which, when warmed to approximately between 50 degrees C. and 105 degrees C., is conformable to a dental arch, the softer base component having a contact surface and a mounting surface, with the contact surface having a center portion shaped to fit against an oral palate and at least one sidewall shaped to fit over the dental arch, and the softer base component being colored to resemble gum tissue; and
a harder component including:
a plurality of tooth-like structures partially embedded in the softer base component and extending beyond the mounting surface of the softer base component, wherein said plurality of tooth-like structures are shaped and colored to resemble teeth, and
a plurality of internal support structures connected to and radially extending from said plurality of tooth-like structures, embedded within the center portion and said at least one sidewall of the softer base component, and each presenting a longitudinal length, wherein the structures are cooperatively configured such that the lengths increase posteriorly,
wherein, when the dental prosthetic device is donned, the dental prosthetic device facilitates biting and chewing in the manner of natural teeth.

10. The dental prosthetic device as set forth in claim 9, wherein the one or more tooth-like structures and the one or more internal support structures are constructed of the same material.

11. The dental prosthetic device as set forth in claim 10, wherein the material is acrylic.

12. The dental prosthetic device as set forth in claim 10, wherein the material is polyethylene.

13. The dental prosthetic device as set forth in claim 10, wherein the material is polycarbonate.

14. The dental prosthetic device as set forth in claim 9, wherein the internal support structures are constructed of a more flexible material than the one or more tooth-like structures.

15. The dental prosthetic device as set forth in claim 9, wherein the one or more tooth-like structures and the one or more internal support structures are molded as a single piece but in such a way as to have different properties, with the one or more internal support structures being more flexible than the one or more tooth-like structures.

16. A dental prosthetic device comprising:
a softer base component constructed of a remoldable thermoplastic material including ethylene vinyl acetate which, when warmed to approximately between 50 degrees C. and 105 degrees C., is conformable to a dental arch, the softer base component having a contact surface and a mounting surface, with the contact surface having a center portion shaped to fit against an oral palate and first and second sidewalls shaped to fit over the dental arch, and the softer base component being colored to resemble gum tissue; and
a harder component including:
one or more tooth-like structures partially embedded in the softer base component and extending beyond the mounting surface of the softer base component, wherein said plurality of tooth-like structures are shaped and colored to resemble teeth, and
one or more internal support structures, with each internal support structure presenting planar ribs, being fixedly connected to and radially extending from one of the one or more tooth-like structures, embedded in and extending at least half-way into the center portion and at least half-way into the first and second sidewalls of the softer base component,
wherein, when the dental prosthetic device is donned, the dental prosthetic device facilitates biting and chewing in the manner of natural teeth.

* * * * *